(12) United States Patent
Walker, Jr.

(10) Patent No.: US 6,509,380 B1
(45) Date of Patent: Jan. 21, 2003

(54) METHOD OF TREATING IRON OVERLOAD WITH ACETAMINOPHEN

(75) Inventor: Ernest M. Walker, Jr., Huntington, WV (US)

(73) Assignee: Marshall University Research Corporation, Huntington, WV (US)

( * ) Notice: Subject to any disclaimer, the term of this patent is extended or adjusted under 35 U.S.C. 154(b) by 0 days.

(21) Appl. No.: 10/014,783

(22) Filed: Dec. 14, 2001

(51) Int. Cl.$^7$ ............................................... A61K 31/16
(52) U.S. Cl. ........................ 514/629; 514/568; 514/575; 514/922; 514/630
(58) Field of Search ................................. 514/568, 575, 514/629, 630, 922

(56) References Cited

U.S. PATENT DOCUMENTS

| | | |
|---|---|---|
| 5,712,098 A | 1/1998 | Tsuchihashi et al. |
| 5,753,438 A | 5/1998 | Drayna et al. |
| 5,780,264 A | 7/1998 | Wessling-Resnick et al. |
| 5,916,910 A | 6/1999 | Lai |
| 5,922,761 A | 7/1999 | Lai |
| 6,093,743 A | 7/2000 | Lai et al. |
| 6,140,305 A | 10/2000 | Thomas et al. |

OTHER PUBLICATIONS

Walker, Jr. et al., "Effects of Iron Overload on the Immune System", *Ann. Clin. Lab. Sci.*, 30 (4), pp. 354–365 (2000).
Carthew et al., "A Unique Rodent Model for Both the Cardiotoxic and Hepatotoxic Effects of Prolonged Iron Overload", *Lab. Invest.*, 69 (2), pp. 217–222 (1993).
Walker, Jr. et al., "Reduction of Murine Iron Overload by Selected Chelating Agents", *Ann. Clin. Lab. Sci.*, 23 (4), p. 316. (1993).
McKie et al., "A Novel Duodenal Iron–Regulated Transporter, IREG1, Implicated in the Basolateral Transfer of Iron to the Circulation", *Molecular Cell*, 5, pp. 299–309 (2000).
Bettigole, "Drugs Acting on the Blood and Blood–Forming Organs", *Textbook of Pharmacology*, Smith ed., Chapter 46, pp. 784–801 (1992).
Meyboom et al., "Metal antagonists", *Meyler's Side Effects of Drugs*, Dukes ed., Chapter 23, pp. 605–625 (1996).
Atkinson, "Nutritional Aspects of Pharmacology", *Human Pharmacology*, Brody et al. eds., Chapter 63, p. 854 (1998).
Hanniger et al., "Hemochromatosis Caused by Excessive Vitamin Iron Intake", *Am. J. Pathology*, 96 (2), pp. 611–618 (1979).
Walker, Jr. et al., "Hereditary Hemochromatosis", *Ann. Clin. Lab. Sci.*, 28 (5), pp. 300–312 (1998).
Walker, Jr. et al., "Comparative Iron Mobilizing Actions of Selected Chelating Agents in Iron–Loaded Mice", *Ann. Clin. Lab. Sci.*, 24 (5), p. 478 (1994).
Gale et al., "Effects of Acetaminophen on Cadmium Metabolism in Mice", *Toxicol. Appl. Pharmaco.*, 82, pp. 368–377 (1986).
Walker, Jr. et al., "Reduction of Iron Overload in an Established Iron–Overloaded Gerbil Model", *Ann. Clin. Lab. Sci.*, (2001).
Walker, Jr. et al., "Use of a Gerbil Model to Study the Effects of Iron–Overloading", *Ann. Clin. Lab. Sci.*, (2001).

*Primary Examiner*—Frederick Krass
(74) *Attorney, Agent, or Firm*—Gary M. Nath; Todd L. Juneau; Joshua B. Goldberg

(57) ABSTRACT

The present invention relates to methods of controlling iron overload in a patient in need thereof. The present invention particularly relates to methods of treating hemochromatosis and other causes of iron overload.

11 Claims, No Drawings

METHOD OF TREATING IRON OVERLOAD WITH ACETAMINOPHEN

FIELD OF THE INVENTION

The present invention relates to methods for reducing iron levels and/or levels of other toxic metals or elements in mammals. In a particular aspect, the present invention relates to methods for reducing free iron ion levels and/or excess and toxic levels of other elements in mammals, and to the removal of excess iron or excesses of other metals/elements stored in the organs by administration of acetaminophen and/or structural or chemical analogues or derivatives thereof. These compounds may scavenge excess iron or free iron ions in hosts undergoing anthracycline chemotherapy, as well as hosts suffering from iron overload or non-iron overload diseases and/or conditions, such as hereditary hemochromatosis, blood-transfusion related anemias and hemolytic anemias such as thalassemia, hemodialysis, stroke, and rheumatoid arthritis. Acetaminophen is particularly preferred in this regard. In a further aspect, the present invention relates to compositions and formulations useful in the methods disclosed herein.

BACKGROUND OF THE INVENTION

Iron is crucial for maintaining normal structure and function of virtually all mammalian cells (see, for example, Voest et al., in *Ann. Intern. Med.*, 120:490–499 (1994) and Kontoghiorghes, G. J., in *Toxicol. Letters*, 80:1–18 (1995), the contents of which are hereby incorporated by reference in their entirety). Iron and its binding proteins have immunoregulatory properties. Adult humans contain 3–5 g of iron, mainly in the form of hemoglobin (58%), ferritin/hemosiderin (30%), myoglobin (9%) and other heme or nonheme enzyme proteins (Harrison and Hoare, in *Metals in Biochemistry*, Chapman and Hall, New York, 1980, the contents of which is hereby incorporated by reference in its entirety). Approximately 10 to 15 mg of dietary iron is normally consumed per day by each individual in the U.S. About 1 to 2 mg of iron in the Fe (II) form is absorbed each day chiefly through villi in the duodenum to compensate for the 1 to 2 mg daily body loss of iron. Normal men absorb about 1 mg iron per day, menstruating women 2 mg iron per day, and hemachromotosis patients 2 to 5 mg iron per day.

Total iron levels in the body are regulated mainly through absorption from the intestine and the erythropoietic activity of the bone marrow. Upon absorption, iron is transported to various tissues and organs by the serum protein transferrin. Once transported to the target tissue or organ, iron is transported and stored intracellularly in the form of ferritin/hemosiderin. Under normal conditions, transferrin is about 30% saturated with iron in healthy individuals, and an equilibrium is maintained between the sites of iron absorption, storage and utilization. The presence of these homeostatic controls ensures the maintenance of physiological levels of not only iron, but also other essential metal ions such as copper, zinc and cobalt. The control of iron absorption may be genetic with complex interactions with intestinal mucosal cells, dietary factors, and other influences.

Iron is absorbed both as heme and non-heme iron chiefly in the duodenum and the proximal jejunum. Iron in meat, primarily heme iron, is better absorbed than non-heme iron. The absorption of heme iron is not influenced by dietary composition or luminal factors as is the absorption of non-heme iron.

Breakdown of these controls could result in metal imbalance and metal overload, causing iron overloading toxicity and possibly death in many groups of patients, especially those with idiopathic hemochromatosis (see, for example, Guyader et al., in *Gastroenterol.*, 97:737–743 (1989), the contents of which is hereby incorporated by reference in its entirety). Shifting of immunoregulatory balances by iron excess or deficiency may produce severe, deleterious psychological effects.

Iron, particularly in the form of free iron ions, can promote the generation of reactive oxygen species through the iron-catalyzed Fenton and Haber-Weiss reactions (Haber and Weiss, in Proc R Soc Ser A 1934;147:332) as follows:

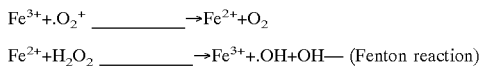

The Haber-Weiss reaction is shown below:

(. designates a free radical, in this case an oxygen free radical)
(modified from U.S. Pat. No. 5,922,761)

The Haber-Weiss and Fenton reactions are seen to produce the hydroxyl radical (.OH), a highly potent oxidant which is capable of causing oxidative damage to lipids, proteins, and nucleic acids (Lai and Piette. Biochem Biophys Res-Commun 1977;78:51–9, and Dizdaroglu and Bergtold. Amal Biochem 1986;156:182).

Effects of iron overload include decreased antibody-mediated and mitogens-stimulated phagocytosis by monocytes and macrophages, alterations in T-lymphocyte subsets, and modification of lymphocyte distribution in different compartments of the immune system. Accordingly, among its toxic effects, iron is known to mediate a repertoire of oxygen related free radical reactions (see, for example, Halliwell and Gutteridge, in Halliwell and Gutteridge, Free Radicals in Biology and Medicine, 2nd edition. Oxford: Clarendon Press, 15–19 (1989), the contents of which is hereby incorporated by reference in its entirety).

The importance of iron in regulating the expression of T-lymphocyte cell surface markers, influencing the expansion of different T-cell subsets, and affecting immune cell functions can be demonstrated in vitro and in vivo. The poor ability of lymphocytes to sequester excess iron in ferritin may help to explain the immune system abnormalities in iron-overloaded patients.

In particular, hemochromatosis is a disease of excessive iron storage leading to tissue damage and fibrosis. Both genetic, or hereditary, hemochromatosis, which can affect 1 in 500 of some populations, and the form of this disease which occurs as a secondary consequence of the hemoglobinopathy, homozygous β-thalassemia, with 40 million carriers worldwide, have a common pathology. The cardiotoxicity and hepatotoxicity, which occurs with this disease, have never been produced experimentally in other species. Hemochromatosis of the liver in man is caused when the iron burden exceeds a threshold in the region of 22 μmol/g liver dry weight.

Genetic hemochromatosis, a life-long disease, is probably the most common autosomal recessive disorder found in white Americans, of whom about 5/1,000 (0.5 percent) are homozygous for the associated gene. The hemochromatosis gene is probably located close to the HLA-A locus on the short arm of chromosome 6. Homozygous individuals may develop severe and potentially lethal hemochromatosis, especially after age 39.

Hereditary hemochromatosis involves an increased rate of iron absorption from the gut with subsequent progressive storage of iron in soft organs of the body. Excessive iron storage eventually produces pituitary, pancreatic, cardiac, spleen, epidermal, and liver and/or hepatic failure or cancer. Damage to these organs may be characterized by elevated liver enzyme values and hepatomegaly often with cirrhosis which may develop into hepatocellular carcinoma, splenomegaly, pancreatic fibrosis leading to diabetes mellitus, hyperpigmentation of the skin, pituitary insufficiency, hypogonadism, occasional hypothyroidism, cardiac abnormalities such as arrythmias and/or congestive heart failure, and arthritis/arthropathy. Early diagnosis can prevent these excess iron-induced problems. Iron overload owing to HLA-linked hereditary hemochromatosis can be distinguished from other causes of hemochromatosis by liver biopsies and interpretations.

Iron overload as seen in hereditary hemochromatosis patients enhances suppressor T-cell (CD8) numbers and activity, decreases the proliferative capacity, numbers, and activity of helper T cells (CD4) with changes in CD8/CD4 ratios, impairs the generation of cytotoxic T cells, and alters immunoglobulin secretion when compared to treated hereditary hemochromatosis patients or controls. A correlation has recently been found between low CD8+ lymphocyte numbers, liver damage associated with HCV positivity, and severity of iron overload in beta-thalassemia major patients. Iron overload, with its associated increases of serum iron levels and transferring saturation, may cause a poor response to interferon therapy. Iron overload with hyperferremia is associated with suppressed functions of the complement system (classic or alternative types).

Cadmium (2+, II) is absorbed from the gastrointestinal tract, but most is absorbed via the lungs, especially in smokers (tobacco contains a lot of cadmium). It is bound chiefly to blood cells and albumin, transported to the liver, and then is redistributed to the kidney as cadmium-metallothionein. Cadmium has a body half-life of 10 to 30 years, so that continuous environmental exposure causes progressive increases in tissue and organ concentrations of cadmium with increasing age, so that a 50-year old man may have a cadmium body burden of 30 mg or more. (Klaassen C D, 1996). Approximately 50% of the body cadmium is stored in the liver and kidneys. Very few chelating agents are available to remove body cadmium. The agent $CaNa_2EDTA$ is used by some. The use of dimercaprol and substituted dithiocarbamates may be useful in treating individuals chronically exposed to cadmium. (Klaassen, 1996; Jones M M, et al. Toxicol Appl Pharmacol 1991;110:241–50).

Lead poisoning is more of a problem in utero during fetal development and in young children, who might eat paint chips containing lead. Lead can cross the placental barrier to produce deleterious effects in the developing fetus. Children absorb lead from the gastrointestinal tract more efficiently than adults. Lead accumulations may result from exposure to inorganic or organic compounds. Acute lead poisoning is relatively rare, but chronic lead poisoning (plumbism) is encountered with signs and symptoms occurring separately or concurrently in the gastrointestinal, neuromuscular, central nervous system, hematological, renal, and other systems. Most body lead is stored in bone, but some is found in other tissues (Klaassen C D, 1996).

Four different chelating agents are used to treat patients with high body burdens of lead: (1) $CaNa_2EDTA$, (2) dimercaprol (BAL), (3) D-penicillamine, and (4) Succimer. Succimer is the first safe, orally effective and active lead chelator for children (Klaassen C D, 1996). Removal of organic lead is more difficult than removal of inorganic lead, since the organic lead must first be converted to inorganic lead prior to removal.

Mercury poisoning continues to be an important problem due to occupational exposure and environmental pollution (Klaassen CD, 1996). Three chemical forms are of concern regarding toxicity: elemental mercury (mercury vapor), inorganic mercury salts, and organic mercurials. Mercury can exist in two different oxidative states: mercurous (+1) salts and mercuric (+2) salts. Overall, organic mercurials are more toxic and can cause serious damage to the central nervous system (Klaassen CD. Ch. 66).

There are two somewhat effective, but not ideal chelating agents available to treat mercurial poisoning: dimercaprol (treatment of symptomatic patients with high mercury levels) and D-penicillamine (asymptomatic patients with low mercury levels). These are used to treat elemental mercury or inorganic mercury poisoning and may be used alone, or in combination. They are usually administered intramuscularly and are not effective when given orally.

Short-term organic mercurials such as methylmercury cause special problems in that they are very difficult to mobilize and eliminate from the body. Dimercaprol may increase methylmercury concentrations in the central nervous system. D-penicillamine reduces mercury levels but its clinical efficacy is not impressive (Klaassen C D, 1996). A polythiol resin appears to reduce the extensive enterohepatic recirculation of methylmercury and facilitates its excretion from the body.

Arsenic is taken into the body as a result of industrial and environmental exposure (soil, water, air). Four chemical forms of arsenic are commonly encountered: elemental, inorganic arsenicals, organic arsenicals, and arsine gas ($AsH_3$). Two oxidative states exist: trivalent (3+) and pentavalent (5+). Toxicity of arsenicals generally increases in the sequence: organic arsenicals $<As^{5+}<As^{3+}<$arsine ($AsH_3$) (Klaassen C D. Ch 66). Pentavalent arsenic uncouples mitochondrial oxidative phosphorylation while trivalent arsenicals, including inorganic arsenite, are sulhydryl agents (react with available —SH groups in proteins and enzymes) (Klaassen C D, 1996). Arsenicals can be toxic to a number of organ systems including the cardiovascular system, gastrointestinal tract, kidneys, skin, bone marrow, central or peripheral nervous systems, liver, lungs, and others. Arsenicals may be carcinogenic or teratogenic. Arsenic poisoning can be acute or chronic, and arsenicals are a common cause of accidental, homicidal, or suicidal poisonings (Klaassen C D, 1996).

Two major chelating agents, dimercaprol (BAL) and D-penicillamine (oral or intramuscular), are available to treat arsenic poisoning. Succimer (2,3-dimercaptisuccinic acid) appears to be very promising for the treatment of poisoning, but does not have FDA approval.

Wilson's disease (hepatolenticular degeneration) is a genetic disease characterized by excess concentrations of body copper. Copper exists in the body in two different oxidation states cuprous (1+) and cupric (2+). Two orally effective chelating agents are available to chelate and remove excess body copper. D-penicillamine is the drug of choice in the treatment of Wilson's disease. However, it may cause serious reactions, including anaphylactic reactions in penicillin-sensitive individuals, it may be toxic to the hematological, renal, and/or pulmonary systems, and induce a variety of cutaneous lesions. In cases of D-penicillamine toxicity, a back-up agent, Trientine (triethylenetetramine dehydrochloride; cuprid) is orally effective and may be substituted for D-penicillamine.

The more common trivalent (3+, III) and the less common hexavalent (6+, VI) forms of chromium are of biological importance in mammals. Chromium intake is from industrial and environmental exposure since chromium, Cr(VI), is an abundant element in the Earth's crust. Corrosive hexavalent chromium can cause chronic ulceration and irritation and perforation of the nasal septum and other body structures in contact with it. Cr(VI) easily crosses cell membranes easily into the circulation after which is may be reduced to Cr(III), which is capable of forming complexes with intracellular macromolecules. Repeated exposure to the skin causes "chrome ulcers" which can be treated by topical ascorbic acid which reduces Cr(VI) to Cr(III). Cr(VI) appears to be toxic to the cardiovascular and pulmonary systems and is carcinogenic possibly (especially pulmonary cancers) due to its reduction to Cr(III), with subsequent generation of reactive intermediates. There is no evidence that systemic chelation therapy is beneficial in chromium poisoning. (Aw TC, 1996).

Aluminum is the most common element in the earth's crust so that acute or chronic poisoning is relatively rare. The most common example of aluminum poisoning in human patients occurs in aluminum-toxic dialysis patients. Desferal® has been successful in removing aluminum excesses from these patients (Aw TC, 1996).

Nickel is found in stainless steel and other alloys. Four chemical forms of nickel are encountered: (1) nickel carbonyl, (2) soluble salts of nickel, (3) insoluble salts of nickel, and (4) metallic nickel. Nickel carbonyl is very toxic. It can be absorbed orally and by inhalation. Acute nickel carbonyl poisoning is characterized by gastrointestinal symptoms, muscle fatigue, convulsions, interstitial pneumonitis, cerebral hemorrhage, and death may occur 4 to 11 days after fatal exposure. Chronic exposure is characterized by allergic response (type I hypersensitivity), nonmalignant respiratory disease or pneumoconiosis which may be fatal, and cancer of the lung and nasal sinuses. Nickel dermatitis is common. The highest risk of nickel exposure is during roasting sulfides or ores in dusty conditions or environment.

Treatment of nickel toxicity and reducing body burden or nickel is accomplished by DMPS, which increases the urinary excretion of nickel and by use of substituted dithiocarbamates (diethyldithiocarbamate or Dithiocarb$^R$, and disulfiram or Antabuse$^R$), which appears to be effective in treating nickel-induced dermatitis and in reducing excess body burdens of nickel.

Manganese is an essential metal in mammalian systems in that it serves as an enzyme cofactor in phosphorylation reactions in the body. Exposure is from industrial uses from dust including exposure to the manganese in certain pesticides. Manganese can be absorbed from the gastrointestinal tract or by pulmonary inhalation. Pulmonary pneumonitis may result from acute exposure. Chronic exposure results from prolonged exposure to manganese. Manganese overload has resulted from prolonged (a year or longer) and excessive dietary intake of manganese (as in super vitamins, etc.) Chronic toxicity is associated with serious consequences and can reach a point where manganese-induced damage is irreversible. Excess manganese concentrates in the basal ganglia of the brain and is associated with extrapyramidal symptoms of progressing severity. Rigidity, bradykinesis, and an intension tremor are the main features in established cases of severe manganese poisoning.

Chelation therapy must be initiated at early stages to prevent manganese-induced toxicity and severe symptoms. Damage from chronic manganese toxicity is essentially irreversible once neurological symptoms appear. $CaNa_2$ edetate has shown success in early treatment but no improvement has been noted in patients with neurological damage. Sodium p-aminosalicylic acid has produced improvement in two cases of chronic manganese poisoning, but its efficacy has not been established (Aw TC, Vale J C. Ch. 8.3.6: *Poisoning from Metals,* Weatherall D J et al., eds. Oxford Textbook of Medicine, $3^{rd}$ ed. Oxford, Oxford University Press. 1996:1105–15).

Cobalt is a relatively nontoxic essential metal which serves as a component of vitamin B12 (cyanocobalamine). Toxic poisoning with cobalt is relatively rare, but can occur. Most exposure is industrial as cobalt is used in steel alloys, magnets, hard metals and is found in ores along with nickel, silver, copper, iron, and other metals. Cobalt is readily absorbed from the gastrointestinal tract and via inhalation. A small portion of absorbed cobalt remains in the body with a half-life of about 2 years. About 43% of body cobalt is found in muscle and additional quantities are found in the liver, kidneys, heart, hair and nails. Acute poisoning produces gastrointestinal disturbances. Chronic poisoning can result from longterm industrial exposure "hard metal" which can produce severe pneumoconiosis, pulmonary interstitial fibrosis, polycythemia, cardiomyopathies, and allergies (often simultaneous allergies to nickel and cobalt). (Aw T C, 1996).

Chelation therapy of cobalt includes DMSA (succimer), Dznc (an experimental agent), DTPA (diethylenetriaminepentaacetic acid, as the sodium salt: $CaNa_3$ pentetate; calcium trisodium pentetate). Testing of these agents has been conducted in animals. To date (1996), there have been no satisfactory human studies performed to test the ability of these agents to mobilize and cause excretion of cobalt.

The numerous medical and industrial and energy uses of radioactive heavy metals have caused a special type of problem. Intake of these radioactive heavy metals or nuclear accidents cause toxicity to body tissues and organs due to ionizing radiation. Therefore, it is imperative to chelate these metals, mobilize and cause elimination from the body as quickly as possible (Klaassen C D, 1996). Examples of radioactive heavy metals include: $^{239}Pu$, $^{137}Cs$, $^{144}Ce$, $^{90}Sr$, and others. A number of factors have made such chelation difficult. $CaNa_2DTPA$ has been effective in removing $^{239}Pu$ (Jones M M et al. Reducing the cancer risk of $^{239}Pu$ by chelation therapy has been noted (Radiat Res 1986;107:296–306). Chelation of other radioactive heavy metals by various chelating agents has met with mixed success.

Accordingly, there is presently a great need for the discovery of orally (po) or parenterally (ip, intraperitoneallly; iv, intravenously) effective agents to mobilize and remove all these heavy metals from their target organs and to facilitate their removal from the body.

Presently, the only drug which has been approved by the FDA for treating hemochromatosis is Desferal® (DF). Unfortunately, Desferal® must be administered parenterally in treating iron overload in patients and is sometimes associated with severe hypotension, shock, urticaria, ocular toxicity including visual dysfunction, auditory nephrotoxicity with hearing loss, and other drug-induced adverse effects. L1 (deferiprone, 1,2-dimethyl-3-hydroxypyridin-4-one), an orally effective iron chelator, is available for patients with thalassemia major, who are unable or unwilling to receive deferoxamine, but L1 has not been approved as an oral iron chelator due to its toxic effects (Kontoghiorghes G J. Toxicol Letters 1995;80:1–18).

A major complication in the therapeutic use of chelators in the propensity of chelators to affect not only the desired metal but also many other essential metals, their associated metabolic pathways and other processes. For example, the treatment with DF and L1 requires zinc supplementation to prevent the occurrence of zinc deficiency diseases (De Virgilis et al. Arch Dis Chil 1988;63;250–5; Al-Refai et al. BLOOD 1992;80:593–9).

Therefore, there is still a need in the art for a new treatment for hemochromatosis capable of controlling iron overload in a human without exhibiting any toxic effects.

SUMMARY OF THE INVENTION

The present invention relates to a method of controlling iron levels in a mammal, comprising:

administering to said mammal an effective amount of a physiologically compatible compound capable of binding free iron ions.

The present invention also relates to a method of controlling iron levels in a mammal, comprising:

administering to said mammal an effective amount of acetaminophen.

The present invention further relates to a method of treating hemochromatosis in a mammal, comprising:

administering to said mammal an effective amount of a physiologically compatible compound capable of binding free iron ions.

The present invention additionally relates to a method of treating iron overload resulting from hemochromatosis or any of other multiple causes of iron overload in a mammal, comprising:

administering to said mammal an effective amount of acetaminophen.

DETAILED DESCRIPTION OF THE INVENTION

Definitions

As used herein, materials that are "physiologically compatible" do not induce any significant side effects. The main effect exerted by these materials is to bind free iron ions.

As employed herein, the phrase "free iron ions" refers to transient iron species which are not stably incorporated into a biological complex (e.g. hemoglobin, ferritin, and the like). Scavengers contemplated for use herein are highly selective for "free iron ions", relative to the other forms of iron present in a physiological system.

As employed herein "substituted alkyl" comprises alkyl groups further bearing one or more substituents selected from hydroxyl, alkoxyl (of a lower alkyl group) mercapto (of a lower alkyl group), substituted or unsubstituted cycloalkyl, substituted or unsubstituted heterocycle, substituted or unsubstituted aryl, substituted or unsubstituted heteroaryl, substituted or unsubstituted aryloxy, halogen, trifluoromethyl, cyano, nitro, nitrone, amino, amido, —C(O)H, acyl, oxyacyl, carboxyl, carbamate, sulfonyl, sulfonamide, sulfuryl, and the like.

As employed herein, "cycloalkyl" refers to cyclic ring-containing groups containing in the range of about 3 up to 8 carbon atoms, and "substituted cycloalkyl" refers to cycloalkyl groups further bearing one or more substituents as set forth above.

As employed herein, "alkenyl" refers to straight or branched chain hydrocarbon groups having at least one carbon—carbon double bond, and having in the range of 2 to 12 carbon atoms, and "substituted alkenyl" refers to alkenyl groups further bearing one or more substituents as set forth above.

As employed herein, "alkynl" refers to straight or branched chain hydrocarbon groups having at least one carbon—carbon triple bond, and having in the range of 2 to 12 carbon atoms, and "substituted alkynyl" refers to alkynyl groups further bearing one or more substituents as set forth above.

As employed herein, "aryl" refers to aromatic groups having in the range of 6 to 14 carbon atoms and "substituted aryl" refers to aryl groups further bearing one or more substituents as set forth above.

As employed herein, "alkylaryl" refers to alkyl-substituted aryl groups and "substituted alkylaryl" refers to alkylaryl groups further bearing one or more substituents as set forth above.

As employed herein, "arylalkyl" refers to aryl-substituted alkyl groups and "substituted arylalkyl" refers to arylalkyl groups further bearing one or more substituents as set forth above.

As employed herein, "arylalkenyl" refers to aryl-substituted alkenyl groups and "substituted arylalkenyl" refers to arylalkenyl groups further bearing one or more substituents as set forth above.

As employed herein, "arylalkynyl" refers to aryl substituted alkynyl groups and "substituted arylalkynyl" refers to arylalkynyl groups further bearing one or more substituents as set forth above.

As employed herein, "aroyl" refers to aryl-carbonyl species such as benzoyl and "substituted aroyl" refers to aroyl groups further bearing one or more substituents as set forth above.

As employed herein, "heterocyclic" refers to cyclic (i.e., ring-containing) groups containing one or more heteroatoms (e.g. N, O, S, or the like) as part of the ring structure, and having in the range of 3 to 14 carbon atoms and "substituted heterocyclic" refers to heterocyclic groups further bearing one or more substituents as set forth above.

As employed herein, "acyl" refers to alkyl-carbonyl species.

As employed herein, "halogen" refers to fluoride, chloride, bromide or iodide atoms.

Methods of the Present Invention

In accordance with the present invention, methods have been developed for the in vivo reduction of free iron ion levels in a subject. The present invention employs a scavenging approach whereby free iron ions are bound in vivo to a suitable physiologically compatible scavenger, i.e., a compound capable of binding free iron ions. The resulting complex renders the free iron ions harmless, and is eventually excreted in the urine of the host. Further in accordance with the present invention, there have been developed compositions and formulations useful for carrying out the above-described methods.

A major complication in the therapeutic use of chelators is the propensity of chelators to affect not only the desired metal but also many other essential metals, their associated metabolic pathways and other processes. Thus, for example, treatment with a chelator requires zinc supplementation to prevent the occurrence of zinc deficiency diseases.

The low-molecular-weight iron pool in serum is thought to be the most labile iron source during chelation therapy. Chelators that remove this low-molecular-weight iron with only a minimal effect on other essential metal contents in the body are highly desirable, particularly for the treatment of transfusion-induced iron overload, as well as iron overload induced by anthracycline anti-cancer agents, inflammatory diseases such as rheumatoid arthritis and multiple sclerosis, and the like.

In accordance with another embodiment of the present invention, there are provided methods for treating animals having elevated circulating or stored levels of free or stored iron. This inventive method compromises: administering to an animal at least one physiologically compatible compound capable of binding free iron or mobilizing stored iron from iron storage organs or tissues. Any such compound would also have the ability to similarly bind or mobilize free or ferritin-bound iron, or iron from other iron-bound complexes from human subjects.

It is additionally considered to be within the scope of the present invention to treat mammal suffering from an overload of metals other than iron. Metals such as cadmium, mercury, lead, and chromium are particularly preferred in this regard.

The presence of elevated iron levels in a subject is associated with a wide range of disease states and/or indications, such as, for example, thalassemia, sickle cell anemia, repeated blood transfusions, hereditary hemochromatosis, secondary hemochromatosis, hereditary spherocytosis, hemodialysis, dietary iron uptake, iatrogenic iron uptake, intramuscular iron dextran, hemolytic disease of the newborn, and the like.

Typically symptoms for people afflicted with hereditary, or Type I, hemochromatosis are diabetes mellitus, heart problems, liver problems, pituitary problems, and adrenal problems. Most patients suffering from severe hereditary hemochromatosis are male. Females, especially premenopausal females, have additional protections against iron overload in their bodies.

Secondary hemochromatosis, or hemosiderosis, typically occurs in mammals with conditions causing the accelerated destruction of red blood cells, such as hemolytic anemias, sickle cell anemia, and thalassemias. Treatment of these conditions may require frequent transfusions of red blood cells, which in turn may be destroyed to release even more iron into the body to be stored in target organs. These multiple transfusions result in the accelerated destruction of red blood cells in individuals with hemolytic anemia, sickle cell anemia, and thalassemia. This secondary hemochromatosis is slightly different from hereditary hemochromatosis. Chelating agents are commonly used to treat secondary hemochromatosis.

One common way of treating a person having hereditary hemochromatosis is through the use of phlebotomy therapy. There remains a need, however, for other types of therapy for treating hereditary hemochromatosis.

Additional indications associated with elevated levels of free iron ions include anthracycline anti-cancer therapy, inflammation, septic shock, toxic shock syndrome, rheumatoid arthritis, ulcerative colitis, inflammatory bowel disease, gastritis, adult respiratory distress syndrome, asthma, cachexia, transplant rejection, myocarditis, multiple sclerosis, diabetes mellitus, autoimmune disorders, eczema, psoriasis, glomerulonephritis, heart failure or severe arryhtmias, heart disease, atherosclerosis, Crohn's disease, dermatitis, urticaria, cerebral ischemia, systemic lupus erythematosis, AIDS, AIDS dementia, chronic neurodegenerative disease, chronic pain, priapism, cystic fibrosis, amyotrophic lateral sclerosis, schizophrenia, depression, premenstrual syndrome, anxiety, addiction, migraine, Parkinson's disease, Huntington's disease, epilepsy, neurodegenerative disorders, gastrointestinal motility disorders, obesity, hyperphagia, ischemia/reperfusion injury, solid tumors (e.g., neuroblastoma), malaria, hematologic cancers, Alzheimer's disease, infection (including bacterial, viral, fungal, and parasitic infections), myelofibrosis, lung injury, graft-versus-host disease, head injury, CNS trauma, cirrhosis, hepatitis, renal failure, liver disease (e.g., chronic hepatitis C), drug-induced lung injury (e.g., paraquat), transplant rejection and preservation, and the like.

With particular reference to cytokine therapy, the present inventive methods will find widespread use because cytokine therapy (with consequent induction of release of free iron ions) is commonly used in the treatment of cancer and AIDS patients. Side effects due to the induction of free iron ion release are problems commonly associated with cytokine therapy (Lissoni et al. J Biol Regulators Hemeostatic Agents 1993;7:31–3). Thus, a large population exists which will benefit from the present inventive methods.

Presently preferred indications for treatment in accordance with the present invention include administration of IL-1, administration of IL-2, administration of IL-6, administration of IL-11, administration of IL-12, administration of tumor necrosis factor, administration of interferon-alpha or interferon-gamma, arthritis, asthma, Alzheimer's disease, Parkinson's disease, multiple sclerosis, cirrhosis or allograft rejection. Especially preferred indications for treatment in accordance with the present invention include release of free iron ions associated with cytokine therapy.

In accordance with a particular aspect of the present invention, the para-aminophenol-containing iron scavenger may be administered in combination with a cytokine (e.g. Il-1, Il-2, IL-6, IL-11, IL-12, TNF, or interferon-gamma), an antibiotic (e.g. gentamicin, tobramycin, amikacin, piperacillin, clindamycin, cefoxitin, vancomycin, or mixtures thereof), antifungal agent such as amphotericin-B, a vasoactive agent (e.g. catecholamine, noradrenalin, dopamine, or dobutamine), or mixtures thereof. In this way, the detrimental side effects of many of the above-described agents can be reduced or prevented by the para-aminophenol-containing iron scavenger. Thus, a patient being treated with any of the above-described agents could be monitored for evidence of elevated free iron ion levels. At the first evidence of such elevated levels of free iron ions, co-administration of a suitable dose of the described para-aminophen or acetaminophen-containing iron scavenger could be initiated, thereby alleviating (or dramatically reducing) the side effects of the primary therapy.

Compounds of the Present Invention

The only drug presently approved by the FDA for treating iron overload is Desferal®. However, Desferal® is toxic at the higher doses usually required to effectively control iron overload in a patient. To remedy this problem, the present invention contemplates combining the use of acetaminophen with the use of Desferal® to control iron overload in a patient.

In accordance with a particular aspect of the present invention, the physiologically compatible compound, or the acetaminophen, is administered in combination with another therapy. In particular, Desferal® is used as another therapy. In this way, the detrimental side effects of the Desferal® can be prevented or reduced by the primary compound administered to the patient.

Compounds contemplated for use in the practice of the present invention include any physiologically compatible structural or chemical analogues of the para-aminophenol (i.e., $NR_1R_2$-benzene-$R_3$; ex. acetaminophen, or other para-aminophenol derivatives or analogues) or aniline ($NR_1R_2$-benzene; ex. acetanilide) moieties, or any metal/nonmetal salts, derivatives, or conjugates of these compounds. In the case of $NR_1R_2$-benzyl-$OR_3$, $R_1$, $R_2$, and $R_3$ can be hydrogen, up to $C_{18}$ alkyl, substituted alkyl, cycloalkyl, substituted cycloalkyl, substituted or unsubstituted heterocycle, substituted or unsubstituted alkenyl, substituted or unsubstituted alkynyl, substituted or unsubstituted aryl, heteroaryl, substituted or unsubstituted arylalkyl, substituted or unsubstituted arylalkenyl, substituted or unsubstituted arylalkynyl, substituted or unsubstituted aroyl, substituted or unsubstituted acyl or $R_1$ and $R_2$ can be taken together to form a 5-, 6-, or 7-membered ring including N, $R_1$, and $R_2$.

Compounds having the above described generic structure are those wherein: $R_1$, $R_2$ and $R_3$=up to $C_{12}$ alkyl, substituted alkyl, substituted or unsubstituted alkenyl, substituted or unsubstituted alkynyl, wherein the substituents are selected from carboxyl, —C(O)H, oxyacyl, phenol, phenoxy, pyridinyl, pyrrolidinyl, amino, amido, hydroxy, nitro, sulfuryl, or others.

Compounds having the above described generic structure are those wherein: $R_1$=a $C_2$ to $C_8$ alkyl or substituted alkyl, wherein the substituents are selected from carboxyl, acetyl, pyridinyl, pyrrolidinyl, amino, amido, hydroxy, or nitro and $R_2$ is selected from a $C_1$ to $C_6$ alkyl or substituted alkyl, or $R_2$ can be taken together with $R_1$ to form a 5-, 6-, or 7-membered ring including N, $R_2$ and $R_1$.

The presently most preferred para-aminophenol compounds, i.e. compounds having the above described generic structure and the best antipyretic/analgesis benefit with the least toxicity are: acetaminophen, where $R_1$=acetyl, $R_2$=H, and $R_3$=H; and phenacetin, where $R_1$=acetyl, $R_2$=H, and $R_3$=ethyl. It is not known if these two agents will also be the most effective of the para-aminophenol compounds regarding the removal of toxic metals.

When $R_1$ and $R_2$ are taken together to form a 5-, 6-, or 7-membered ring, the combination of $R_1$ and $R_2$ can be a variety of saturated or unsaturated 4, 5, or 6 atom bridging species selected from alkenylene or —O—, —S—, —C(O)—, and/or —N(R)-containing alkylene moieties, wherein R is hydrogen or a lower alkyl moiety.

Included in these compounds are those in which the benzene ring has been replaced by saturated cyclobutane, cyclopentane, cyclohexane, or cycloheptane rings.

Route of Administration

Those of skill in the art recognize that the compounds described herein can be delivered in a variety of ways, such as, for example, orally, parenterally (intravenously or intraperitoneally), subcutaneously, rectally, by inhalation, and the like.

Since individual subjects may present a wide variation in severity of symptoms and each drug has its unique therapeutic characteristics, the precise mode of administration and dosage employed for each subject is left to the discretion of the practitioner. In general, the dosage employed in the practice of the present invention falls in the range of about 5 mg–18.5 g/day. The presently preferred mode of administration is oral.

In accordance with still another embodiment of the present invention, there are provided physiologically active composition(s) comprising a compound as described above in a suitable vehicle rendering said compound amenable to oral delivery, transdermal delivery, intravenous delivery, intramuscular delivery, topical delivery, nasal delivery, and the like. Depending on the mode of delivery employed, the compound can be delivered in a variety of pharmaceutically acceptable forms. For example, the compound can be delivered in the form of a solid, solution, emulsion, dispersion, micelle, liposome, and the like.

Pharmaceutical compositions of the present invention can be used in the form of a solid, a solution, an emulsion, a dispersion, a micelle, a liposome, and the like, wherein the resulting composition contains one or more of the compounds of the present invention, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. The active compound is included in the pharmaceutical composition in an amount sufficient to produce the desired effect upon the process or condition of diseases.

Pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations.

Tablets containing the active ingredient in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin.

They may also be in the form of soft gelatin capsules wherein the active ingredient is mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium For this purpose any bland fixed oil may be employed including synthetic mono- or diglycerides, fatty acids (including oleic acid), naturally occurring vegetable oils like sesame oil, coconut oil, peanut oil, cottonseed oil, etc, or synthetic fatty vehicles like ethyl oleate or the like. Buffers, preservatives, antioxidants, and the like can be incorporated as required.

Compounds contemplated for use in the practice of the present invention may also be administered in the form of suppositories for rectal administration of the drug. These compositions may be prepared by mixing the drug with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, it is up to the practitioner to determine a subject's response to treatment and vary the dosages accordingly.

Typical daily doses, in general, lie within the range of from about 80 $\mu$g up to about 300 mg per kg body weight, and, preferably within the range of from 100 $\mu$g to 10 mg per kg body weight and can be administered up to four times daily. The typical daily IV dose lies within the range of from about 10 $\mu$g to about 100 mg per kg body weight, and, preferably, within the range of from 50 $\mu$g to 10 mg per kg body weight.

Mechanisms of Action

Iron Removal

There are several possible mechanisms through which acetaminophen can be effective for controlling iron overload and treating hemochromatosis. One possible mechanism involves the use of acetaminophen to effect the transformation of $Fe^{+3}$ in the body to a $Fe^{+2}$ complex.

In particular, iron is stored in the body chiefly in its ferric ($Fe^{+3}$) form. When administered to a mammal, acetaminophen is metabolized by one of two pathways. The first, non-toxic, pathway does not adversely affect the liver. In the second, toxic, pathway, acetaminophen forms a reactive species having an extra electron which can form covalent bonds. This species can react with membranes and macromolecules in various cells (e.g. liver cells) throughout the body to effectively kill these cells. However, this toxic product reacts with the excessive $Fe^{+3}$ present in the body to form a non-toxic ferrous ($Fe^{+2}$) complex, typically present in bone marrow.

It was initially believed that acetaminophen would be more toxic in iron overloaded animals than in animals having normal iron levels. Multiple tests have shown, however, that acetaminophen is actually less toxic in animals having an iron overload than in animals having normal iron levels.

In a second proposed mechanism of action, acetaminophen, and/or at least some of its chemical analogues, effectively removes iron from multiple tissues, including liver, spleen, pancreas, heart, skin, and endocrine glands such as pituitary and adrenal, whether acetaminophen is given orally, parenterally (intraperitoneally or intravenously), or intramuscularly. Chemical analogues of acetaminophen may share this ability to reduce the body burden of iron.

In yet another proposed mechanism of action, combinations of acetaminophen or its chemical analogues with Desferal®, and/or L1 (1,2-dimethyl-3-hydroxypyrid-4-one), and/or (ICRF-187), and/or a substituted dithiocarbamate (any of those described in U.S. Pat. No. 5,922,761) will produce additive or synergistic reductions in the body burden of iron (more effective that that produced by Desferal®, L1, ICRF-187, or a substituted dithiocarbamate, when used alone) by removing or mobilizing excess iron from organs and tissues, followed by promotion of iron excretion. These combinations might allow the use of lower doses of any effective, but toxic chelating agents or iron-removing agents by maintaining iron-removing effectiveness, while reducing toxicity.

In still another proposed mechanism of action, acetaminophen or one of its chemical analogues used alone or in combination with Desferal® and/or L1, and/or a substituted dithiocarbamate will enhance the iron-removing ability of therapeutic phlebotomies, especially in the latter stages of phlebotomy treatment and during phlebotomy maintenance phases (keep iron at/or near normal levels after excess iron has been removed). This concept results from treatment results obtained in the Mongolian gerbil iron-overload model described below, which very closely simulates the excess iron-induced characteristics of hereditary hemochromatosis seen in human patients.

Cadmium Removal

In one proposed mechanism, acetaminophen, or some of its chemical analogues, can effectively remove cadmium after acute or chronic exposure to or from organs in which cadmium is stored (chiefly liver and kidneys), whether the acetaminophen is given orally, parenterally (intravenously or intraperitoneally), or intramuscularly. Chemical analogues of acetaminophen may share this ability to reduce body burdens of cadmium.

In another proposed mechanism, combinations of acetaminophen or a chemical analogue with $CaNa_2EDTA$ and/or dimercaprol (BAL) and/or a substituted dithiocarbamate (any of those described in U.S. Pat. No. 5,922,761) will produce additive or synergistic reductions in the body burden of cadmium (more effective than those produced by $CaNa_2EDTA$, BAL, or substituted dithiocarbamates, when used alone) by removing or mobilizing cadmium from organs and tissues, followed by promotion of cadmium excretion. These combinations might allow the use of lower doses of the above chelating agents or cadmium-removing agents by maintaining cadmium-removing effectiveness while reducing toxicity.

Lead Removal

In one proposed mechanism, acetaminophen, or some of its chemical analogues, can effectively remove lead after acute exposure to or from organs in which lead is stored (chiefly bone), whether acetaminophen is given orally, parenterally (intravenously or intraperitoneally), or intramuscularly. Chemical analogues of acetaminophen may share this ability to reduce body burdens of lead.

In another proposed mechanism, combinations of acetaminophen, or chemical analogues thereof, with calcium disodium EDTA ($CaNa_2EDTA$), and/or dimercaprol (BAL), and/or D-penicillamine, and/or a substituted dithiocarbamate (including any of those described in U.S. Pat. No. 5,922,761) will produce additive or synergistic reductions in the body burden of lead in acute or chronic lead toxicity cases (more effective that that produced by $CaNa_2EDTA$, BAL, D-penicillamine, or a substituted dithiocarbamate, when used alone) by removing or mobilizing of excess lead from organs and tissues, especially bone, followed by promotion of lead excretion. These combinations might allow the use of lower, but still effective doses of toxic lead-chelating agents or lead-removing agents by maintaining lead-removing effectiveness, while reducing toxicity.

Mercury Removal

In one proposed mechanism, acetaminophen, or a chemical analogue thereof, can effectively remove elemental or inorganic mercury after acute exposure to or from organs in which mercury is stored, whether the acetaminophen is given orally, parenterally (intravenously or intraperitoneally), or intramuscularly. Chemical analogues of acetaminophen may share this ability to reduce body burdens of elemental or inorganic mercury.

In another proposed mechanism, combinations of acetaminophen, or a chemical analogue thereof, with dimercaprol (BAL), and/or D-penicillamine, and/or a substituted dithiocarbamate (including any of those described in U.S. Pat. No. 5,922,761) will produce additive or synergistic reductions in the body burden of elemental or inorganic mercury in acute or chronic mercurial toxicity cases (more effective that that produced by dimercaprol, D-penicillamine, or a substituted dithiocarbamate, when used alone) by removing or mobilizing of excess elemental or inorganic mercury from organs and tissues, followed by promotion of mercury excretion. These combinations might allow the use of lower, but still effective, doses of toxic mercury-chelating agents or mercury-removing agents by maintaining mercury-removing effectiveness, while reducing toxicity.

In yet another proposed mechanism, combinations of acetaminophen or a chemical analogue thereof with dimercaprol (BAL), and/or D-penicillamine, and/or a substituted dithiocarbamate, and/or a polythiol resin capable of reducing extensive enterohepatic recirculation of organic mercurials (such as methylmercury) will produce additive or synergistic reductions in the body burden of organic mercury in acute or chronic organo-mercurial toxicity cases (more effective that that produced by dimercaprol, D-penicillamine, a substituted dithiocarbamate, or an organomercurial-removing polythiol resin, when used alone) by removing or mobilizing of excess organo-mercurial compounds from organs and tissues, followed by promotion of organo-mercurial excretion. These combinations might allow the use of lower, but still effective doses of toxic mercury-chelating agents or mercury-removing agents by maintaining organo-mercurial-removing effectiveness, while reducing toxicity.

Arsenic Removal

In one proposed mechanism, acetaminophen, or a chemical analogue thereof, can effectively remove arsenic after acute exposure to or from organs in which arsenic is stored, whether the acetaminophen is given orally, parenterally (intravenously or intraperitoneally), or intramuscularly. Chemical analogues of acetaminophen may share this ability to reduce body burdens of arsenic.

In another proposed mechanism, combinations of acetaminophen or a chemical analogue thereof with dimercaprol (BAL), and/or D-penicillamine, and/or a substituted dithiocarbamate (including any of those described in U.S. Pat. No. 5,922,761) will produce additive or synergistic reductions in the body burden of arsenic in acute or chronic arsenic toxicity cases (more effective that that produced by dimercaprol, D-penicillamine, or a substituted dithiocarbamate, when used alone) by removing or mobilizing of excess arsenic from organs and tissues, followed by promotion of arsenic excretion. These combinations might allow the use of lower, but still effective doses of toxic arsenic-chelating agents or arsenic-removing agents by maintaining arsenic-removing effectiveness, while reducing toxicity.

Copper Removal

In one proposed mechanism, acetaminophen, or a chemical analogue thereof, can effectively remove excess copper in patients with Wilson's disease from organs in which the excess copper is stored (chiefly liver), whether the acetaminophen is given orally, parenterally (intravenously or intraperitoneally), or intramuscularly. Chemical analogues of acetaminophen may share this ability to reduce body burdens of copper.

In another proposed mechanism, combinations of acetaminophen or a chemical analogue thereof with D-penicillamine and/or its back-up chelating agent, trientine, will produce additive or synergistic reductions in the body burden of copper in acute or chronic copper toxicity, such as that seen in cases of Wilson's disease (more effective that that produced by D-penicillamine, or trientine, when used alone) by removing or mobilizing excess copper from target organs and tissues, followed by promotion of copper excretion. These combinations might allow the use of lower, but still effective, doses of toxic copper-chelating agents or copper-removing agents by maintaining copper-removing effectiveness, while reducing toxicity.

Chromium Removal

In one proposed mechanism, acetaminophen, or a chemical analogue thereof, can effectively remove excess chromium in patients from organs or tissues in which the excess chromium exists, whether the acetaminophen is given orally, parenterally (intravenously or intraperitoneally), intramuscularly, or topically to treat chrome ulcers). Chemical analogues of acetaminophen may share this ability to reduce body burdens of excess chromium, or treat chromium-induced skin lesions.

In another proposed mechanism, combinations of acetaminophen or a chemical analogue thereof with ascorbic acid will be superior to either agent alone, in treating or resolving chrome ulcers or similar chromium-associated skin lesions.

Aluminum Removal

In one proposed mechanism, acetaminophen, or a chemical analogue thereof, can effectively remove excess aluminum in patients (especially aluminum-toxic dialysis patients) from organs or tissues in which the excess aluminum exists, whether the acetaminophen is given orally, parenterally (intravenously or intraperitoneally), or intramuscularly. Chemical analogues of acetaminophen may share this ability to reduce body burdens of excess aluminum.

In another proposed mechanism, combinations of acetaminophen or a chemical analogue with Desferal® will produce additive or synergistic reductions in the body burden of aluminum in acute or chronic aluminum toxicity, such as that seen in cases of aluminum-toxic dialysis patients (more effective that that produced by Desferal®, when used alone) by removing or mobilizing excess aluminum from target organs and tissues, followed by promotion of aluminum excretion. These combinations might allow the use of lower, but still effective doses of Desferal® as an aluminum-chelating or aluminum-removing agent by maintaining aluminum-removing effectiveness, while reducing toxicity.

Nickel Removal

In one proposed mechanism, acetaminophen, or a chemical analogue thereof, can effectively remove excess nickel in patients (those with nickel-induced dermatitis or with high systemic body burdens of nickel) from organs or tissues in which the excess nickel exists, whether the acetaminophen is given orally, parenterally (intravenously or intraperitoneally), or intramuscularly. Chemical analogues of acetaminophen may share this ability to reduce body burdens of excess nickel or prove to be effective in treating nickel-induced dermatitis.

In another proposed mechanism, combinations of acetaminophen or a chemical analogue thereof with substituted dithiocarbamates (Dithiocarb®, disulfiram, or any of those described in U.S. Pat. No. 5,922,761) and/or DMPS will produce additive or synergistic reductions in the body burden of nickel in acute or chronic nickel toxicity, such as that seen in cases of nickel dermatitis or increased systemic body burdens of nickel (more effective that that produced by Dithiocarb® disulfiram or other substituted dithiocarbamate, and/or DMPS, when used alone) by removing or mobilizing excess nickel from target organs and tissues, followed by promotion of nickel excretion. These combinations might allow the use of lower, but still effective doses of Dithiocarb®, or other substituted dithiocarbamate, or DMPS as a nickel-chelating or nickel-removing agent by maintaining nickel-removing effectiveness, while reducing toxicity.

Manganese Removal

In one proposed mechanism, acetaminophen, or a chemical analogue thereof, can effectively remove excess manganese in patients (especially early cases in which those without manganese-induced neurological damage or symptoms or with high systemic body burdens of manganese) from organs or tissues in which the excess manganese (such as basal ganglia of brain) exists, whether the acetaminophen is given orally, parenterally (intravenously or intraperitoneally), or intramuscularly. Chemical analogues of acetaminophen may share this ability to reduce body burdens of excess manganese or prove to be effective in treating or preventing manganese-induced toxicity and symptoms.

In another proposed mechanism, combinations of acetaminophen or a chemical analogue thereof with substituted $CaNa_2$ EDTA and/or sodium p-aminosalicylic acid will produce additive or synergistic reductions in the body burden of manganese in acute or chronic manganese toxicity, such as that seen in cases of manganese-induced pulmonary or neurological toxicity or increased systemic body burdens of manganese (more effective that that produced by $CaNa_2$ EDTA or sodium p-aminosalicylic acid, when used alone) by removing or mobilizing of excess manganese from target organs and tissues, followed by promotion of manganese excretion. These combinations might allow the use of lower, but still effective, doses of $CaNa_2$ EDTA or sodium p-aminosalicylic acid by enhancing their manganese-chelating or manganese-removing potential by maintaining manganese-removing effectiveness, while reducing toxicity.

Cobalt Removal

In one proposed mechanism, acetaminophen, or a chemical analogue thereof, can effectively remove excess cobalt in patients with cobalt-induced cardio-pulmonary complications or with high systemic body burdens of cobalt from organs or tissues in which the excess cobalt exists, whether the acetaminophen is given orally, parenterally (intravenously or intraperitoneally), or intramuscularly. Chemical analogues of acetaminophen may share this ability to reduce body burdens of excess cobalt or prove to be effective in treating cobalt-induced complications.

In another proposed mechanism, combinations of acetaminophen or a chemical analogue thereof with substituted DMSA (Succimer) and/or DTPA ($CaNa_3$ pentetate) will produce additive or synergistic reductions in the body burden of cobalt in acute or chronic cobalt toxicity, such as that seen in cases of cobalt-induced cardiopulmonary pathology and symptoms, or increased systemic body burdens of cobalt (more effective than that produced by DMSA or DTPA, when used alone) by removing or mobilizing excess cobalt from target organs and tissues, followed by promotion of cobalt excretion. These combinations might allow the use of lower, but still effective, doses of DMSA, or DTPA as a cobalt-chelating or cobalt-removing agent by maintaining cobalt-removing effectiveness, while reducing toxicity.

Radioactive Heavy Metal Removal

In one proposed mechanism, acetaminophen, or a chemical analogue thereof, can effectively remove excesses of one or more of the radioactive heavy metals in patients (those with high body burdens of a radioactive heavy metal or victims of nuclear accidents) from organs or tissues in which the excess radioactive heavy metal exists, whether the acetaminophen is given orally, parenterally (intravenously or intraperitoneally), or intramuscularly. Chemical analogues of acetaminophen may share this ability to reduce body burdens of excess radioactive heavy metals cobalt or prove to be effective in treating or preventing radioactive-heavy-metal-induced complications.

In another proposed mechanism, combinations of acetaminophen or a chemical analogue thereof with $CaNa_3$ pentetate or a calcium trisodium salt of diethylenetriaminepentaacetic acid will produce additive or synergistic reductions in the body burden of $^{239}Pu$ in acute or chronic toxicity, such as that seen in cases of poisoning or nuclear accidents involving $^{239}Pu$ more effective that that produced by DTPA, when used alone, by removing or mobilizing of excess $^{239}Pu$ from target organs and tissues, followed by promotion of excretion. These combinations might allow the use of lower, but still effective, doses of DTPA as a $^{239}Pu$-chelating or $^{239}Pu$-removing agent by maintaining $^{239}Pu$-removing effectiveness, while reducing toxicity.

In yet another proposed mechanism, combinations of acetaminophen or a chemical analogue thereof with appropriate other chelating agents will produce additive or synergistic reductions in the body burden of other Radioactive Heavy Metals in acute or chronic toxicity, such as that seen in cases of poisoning or nuclear accidents involving different radioactive heavy metals (more effective that that produced by the chelating agent, when used alone) by removing or mobilizing excess radioactive heavy metals from target organs and tissues, followed by promotion of excretion.

These combinations might allow the use of lower, but still effective doses of the chelating agent or enhance the effectiveness of the chelating agent in removing and causing the excretion of the radioactive heavy metal while reducing toxicity.

EXAMPLES

The following examples are illustrative of the present invention and are not intended to be limitations thereon.

Example 1

Female Mongolian gerbils were divided into groups: positive iron control (iron injections given), iron-treated (injections of iron and acetaminophen), negative iron controls (no iron given), and treatment controls (injections of the investigational agent, only). Gerbils designated to receive iron were iron overloaded by a series of intraperitoneal (ip) injections of iron dextran during a two-month period of time. Treatments were initiated one month after completion of iron overloading and continued for one additional month.

Electrocardiograms (ECGs) were done on gerbils in all four groups, two months and again three months after completion of iron overloading. Gerbils were autopsied five months after completion of iron overloading and resulting stained tissue slides were evaluated by light microscopy. Livers and whole hearts were obtained from gerbils in control and iron-overloaded groups and weighed. Whole hearts and weighed liver samples were acid digested and measured for total iron content.

EKG findings revealed premature ventricular complexes in four of 10 iron-overloaded gerbils (40%) but not in animals from the other three groups. Eight of 20 iron-overloaded gerbils died within 5 months after iron overloading, most likely due to cardiac and/or liver failure. No deaths occurred in the treatment or control groups. Autopsies, coupled with weight data and histological evaluations suggested that the treatment agent effectively combats iron-induced cardiac and hepatic hypertrophy, as judged from treatment-induced reductions in heart weights, heart/total body weight ratios, liver weights, and liver/total body weight ratios.

Treatment greatly reduced accumulations of iron in the bone marrow, proximal renal tubules, heart, and in numerous other organs and tissues, but less than in the livers. Inductively coupled plasma-atomic emission livers. Inductively coupled plasma-atomic emission spectrometry (ICP-AES) tissue iron measurements revealed that treatment reduced cardiac iron over 40% (almost entirely from cardiomyocytes, less from cardiac macrophages) ($P<0.005$), but the 17% reduction in liver iron was not statistically significant from values in untreated, iron-overloaded animals.

The invention being thus described, it will be obvious that the same may be varied in many ways. Such variations are not to be regarded as a departure from the spirit and scope of the invention and all such modifications are intended to be included within the scope of the following claims.

I claim:

1. A method of controlling iron overload in a mammal in need thereof, comprising:
   administering to said mammal an effective amount of acetaminophen for controlling iron overload in said mammal.

2. The method of claim 1, wherein the iron overload causes hemochromatosis in the mammal.

3. The method of claim 2, wherein the hemochromatosis is hereditary hemochromatosis.

4. The method of claim 2, wherein the hemochromatosis is secondary hemochromatosis (hemosiderosis).

5. The method of claim 1, wherein the acetaminophen is administered in combination with an additional agent effective for controlling iron overload.

6. The method of claim 5, wherein the additional agent effective for controlling iron overload is deferoxamine mesylate.

7. A method of treating hemochromatosis in a mammal in need thereof, comprising: administering to said mammal an effective amount of acetaminophen for treating hemochromatosis in said mammal.

8. The method of claim 7, wherein the hemochromatosis is hereditary hemochromatosis.

9. The method of claim 7, wherein the hemochromatosis is secondary hemochromatosis (hemosiderosis).

10. The method of claim 7, wherein the acetaminophen is administered in combination with an additional agent effective for controlling iron overload.

11. The method of claim 10, wherein the additional agent effective for controlling iron overload is deferoxamine mesylate.

* * * * *